United States Patent
Durairaj et al.

(10) Patent No.: US 6,531,637 B1
(45) Date of Patent: Mar. 11, 2003

(54) RESORCINOL PRODUCTION FROM THE HYDROLYSIS OF META-PHENYLENEDIAMINE

(75) Inventors: Raj B. Durairaj, Monroeville, PA (US); Gary A. Jesionowski, Pittsburgh, PA (US)

(73) Assignee: Indspec Chemical Corporation, Pittsburgh, PA (US)

( * ) Notice: Subject to any disclaimer, the term of this patent is extended or adjusted under 35 U.S.C. 154(b) by 0 days.

(21) Appl. No.: 10/033,060

(22) Filed: Dec. 27, 2001

(51) Int. Cl.$^7$ ............................................... C07C 37/00
(52) U.S. Cl. ..................................................... 568/767
(58) Field of Search .......................................... 568/767

(56) References Cited

U.S. PATENT DOCUMENTS

| | | | |
|---|---|---|---|
| 3,462,497 A | | 8/1969 | Greco |
| 3,862,245 A | | 1/1975 | Greco |
| 3,862,246 A | | 1/1975 | Greco |
| 3,937,741 A | * | 2/1976 | Greco |
| 4,118,586 A | * | 10/1978 | Goldstein |

FOREIGN PATENT DOCUMENTS

| | | | |
|---|---|---|---|
| GB | 1205715 | * | 9/1970 |
| JP | 52-153919 | * | 12/1977 |

* cited by examiner

*Primary Examiner*—Michael L. Shippen
(74) *Attorney, Agent, or Firm*—Debra Z. Anderson; Eckert Seamans Cherin & Mellott, LLC (57) ABSTRACT

A process for the preparation of resorcinol using the meta-phenylenediamine hydrolysis reaction is provided. A reactor vessel made of a suitable material such as zirconium or a zirconium alloy is used, thus resisting corrosion and formation of resinous materials.

11 Claims, 7 Drawing Sheets

Figure 1: Two Pass MPDA Hydrolysis Reaction

Figure 2

| Example | 2 | 3 | 4 | 5 | 6 | 7 | 8 |
|---|---|---|---|---|---|---|---|
| ZIRCONIUM REACTOR FEED (g) | | | | | | | |
| MPDA | 44.3 | 36.6 | 55.4 | 54.6 | 43.3 | 35.9 | 35.9 |
| $H_2SO_4$ | 64.4 | 53.2 | 90.5 | 99.1 | 78.7 | 65.2 | 65.2 |
| $H_2O$ | 591.3 | 610.2 | 554.1 | 546.2 | 578 | 598.9 | 598.9 |
| MPDA/$H_2SO_4$/$H_2O$ (mole ratio) | 1/1.6/80 | 1/1.6/100 | 1/1.8/60 | 1/2/60 | 1/2/80 | 1/2/100 | 1/2/100 |
| | | | | | | | |
| SINGLE PASS REACTION CONDITIONS | | | | | | | |
| Temperature (°C) | 200 | 200 | 200 | 200 | 200 | 200 | 200 |
| Time (hrs) | 6 | 2 | 6 | 2 | 4 | 2 | 6 |
| | | | | | | | |
| REACTION MIXTURE | | | | | | | |
| PH | 0.69 | 0.81 | 0.42 | 0.25 | 0.41 | 0.51 | 0.54 |
| Insoluble tars in the reactor (g) | 0 | 0 | 0 | 0 | 0 | 0 | 0 |
| Observation of insoluble tars (if present) | NA | NA | NA | NA | NA | NA | NA |
| | | | | | | | |
| CRUDE RESORCINOL | | | | | | | |
| Weight (g) | 27.2 | 5.8 | 34.9 | 5.3 | 12.1 | 3.1 | 15.7 |
| Resorcinol content (wt%, by NMR) | 91.6 | 94.2 | 95.6 | 97.4 | 96.8 | 97.7 | 97.4 |
| Soluble tar content (wt%, by NMR) | 8.3 | 5.7 | 4.4 | 2.5 | 3.1 | 2.2 | 2.5 |
| Resorcinol yield (wt%) | 55.2 | 14.7 | 59.1 | 9.3 | 26.5 | 8.3 | 41.8 |
| | | | | | | | |
| AQUEOUS PHASE ANALYSIS | | | | | | | |
| ORGANIC MATERIALS (wt%, by NMR) | | | | | | | |
| Resorcinol | ND | ND | ND | ND | ND | ND | ND |
| m-Phenylenediamine | 0.5 | 2.1 | 0.4 | 3.1 | 1.2 | 2.3 | 0.5 |
| m-Aminophenol | 1 | 2 | 2 | 3.5 | 3 | 2.2 | 2.1 |
| Soluble tar | 1.2 | 0.6 | 0.8 | 0.4 | 0.5 | 0.2 | 0.4 |
| INORGANIC MATERIALS | | | | | | | |
| Ammonium bisulfate (wt%) | 12.8 | 11.7 | 19.9 | 19.3 | 19.7 | 17.2 | 15.4 |
| Ammonium sulfate (wt%) | 2.6 | 3.1 | 2.2 | 3.5 | 0.6 | 2.1 | <0.5 |

NA = Not Applicable
ND = None Detected

Figure 3

| Example | 9 | 10 | 11 | 12 |
|---|---|---|---|---|
| ZIRCONIUM REACTOR FEED (g) | | | | |
| MPDA | 56.2 | 36.6 | 43.8 | 54.6 |
| $H_2SO_4$ | 81.6 | 53.2 | 71.6 | 99.1 |
| $H_2O$ | 562.2 | 610.2 | 584.6 | 546.2 |
| $MPDA/H_2SO_4/H_2O$ (mole ratio) | 1/1.6/60 | 1/1.6/100 | 1/1.8/80 | 1/2/60 |
| SINGLE PASS REACTION CONDITIONS | | | | |
| Temperature (°C) | 215 | 215 | 215 | 215 |
| Time (hrs) | 4 | 6 | 2 | 6 |
| REACTION MIXTURE | | | | |
| pH | 0.59 | 0.84 | 0.55 | 0.32 |
| Insoluble tars in the reactor (g) | 1.05 | 1 | 0 | 0 |
| Observation of insoluble tars (if present) | dark orange residue | dark orange residue | NA | NA |
| CRUDE RESORCINOL | | | | |
| Weight (g) | 41.5 | 29 | 21.2 | 49.2 |
| Resorcinol content (wt%, by NMR) | 93 | 94.6 | 94.4 | 98.8 |
| Soluble tar content (wt%, by NMR) | 6.9 | 5.3 | 5.5 | 1.2 |
| Resorcinol yield (wt%) | 67.4 | 73.6 | 44.8 | 87.4 |
| AQUEOUS PHASE ANALYSIS | | | | |
| ORGANIC MATERIALS (wt%, by NMR) | | | | |
| Resorcinol | ND | ND | ND | ND |
| $m$-Phenylenediamine | 0.4 | 0.3 | 0.7 | 0.1 |
| $m$-Aminophenol | 0.6 | 0.3 | 2.1 | 0.8 |
| Soluble tar | 1.1 | 0.6 | 0.7 | 0.3 |
| INORGANIC MATERIALS | | | | |
| Ammonium bisulfate (wt%) | 16.1 | 9.5 | 16.4 | 17.9 |
| Ammonium sulfate (wt%) | 4.1 | 2.4 | 1.5 | 5.5 |

NA = Not Applicable
ND = None Detected

Figure 4

| Example | 13 | 14 | 15 | 16 | 17 | 18 | 19 | 20 |
|---|---|---|---|---|---|---|---|---|
| ZIRCONIUM REACTOR FEED (g) | | | | | | | | |
| MPDA | 56.2 | 56.2 | 36.6 | 55.4 | 36.3 | 54.6 | 43.3 | 35.9 |
| H$_2$SO$_4$ | 81.6 | 81.6 | 53.2 | 90.5 | 59.2 | 99.1 | 78.7 | 65.2 |
| H$_2$O | 562.2 | 562.2 | 610.2 | 554.1 | 604.5 | 546.2 | 578 | 598.9 |
| MPDA/H$_2$SO$_4$/H$_2$O (mole ratio) | 1/1.6/60 | 1/1.6/60 | 1/1.6/100 | 1/1.8/60 | 1/1.8/100 | 1/2/60 | 1/2/80 | 1/2/100 |
| SINGLE PASS REACTION CONDITIONS | | | | | | | | |
| Temperature (°C) | 230 | 230 | 230 | 230 | 230 | 230 | 230 | 230 |
| Time (hrs) | 2 | 6 | 2 | 4 | 6 | 2 | 6 | 2 |
| REACTION MIXTURE | | | | | | | | |
| pH | 0.59 | 0.62 | 0.81 | 0.39 | 0.68 | 0.28 | 0.46 | 0.54 |
| Insoluble tars in the reactor (g) | 3.5 | 3.3 | 0.3 | 0.92 | 0.32 | 0 | 0.08 | 0 |
| Observation of insoluble tars (if present) | heavy red/orange residue | dark red tarry residue | thin layer orange residue | heavy dark red residue | dark orange residue | NA | NA | NA |
| CRUDE RESORCINOL | | | | | | | | |
| Weight (g) | 41.4 | 48.4 | 26.7 | 51.6 | 34 | 45.3 | 42.6 | 29.1 |
| Resorcinol content (wt%, by NMR) | 93.1 | 97.3 | 94.4 | 98.3 | 98.5 | 98.3 | 99.8 | 98.3 |
| Soluble tar content (wt%, by NMR) | 6.8 | 2.7 | 5.5 | 1.6 | 1.5 | 1.7 | 0.2 | 1.7 |
| Resorcinol yield (wt%) | 67.3 | 82.2 | 67.6 | 89.9 | 90.7 | 80 | 96.3 | 78.2 |
| AQUEOUS PHASE ANALYSIS | | | | | | | | |
| ORGANIC MATERIALS (wt%, by NMR) | | | | | | | | |
| Resorcinol | ND | ND | ND | ND | ND | ND | ND | ND |
| m-Phenylenediamine | 0.3 | 0.1 | 0.4 | 0.1 | 0.1 | 0.1 | ND | 0.1 |
| m-Aminophenol | 0.6 | 0.3 | 0.4 | 0.3 | 0.1 | 1.2 | 0.2 | 0.8 |
| Soluble tar | 1 | 0.5 | 0.7 | 0.3 | 0.3 | 0.3 | 0.2 | 0.3 |
| INORGANIC MATERIALS | | | | | | | | |
| Ammonium bisulfate (wt%) | 14.6 | 12.2 | 9.6 | 16.2 | 10.3 | 20.7 | 14.8 | 13.6 |
| Ammonium sulfate (wt%) | 4.1 | 5.6 | 2.7 | 4.4 | 2 | 2 | 3.2 | 1.4 |

NA = Not Applicable
ND = None Detected

Figure 5

| Example | 21 | 22 | 23 |
|---|---|---|---|
| ZIRCONIUM REACTOR FEED (g) | | | |
| MPDA | 54.6 | 54.6 | 54.6 |
| $H_2SO_4$ | 99.1 | 99.1 | 99.1 |
| $H_2O$ | 546.2 | 546.2 | 546.2 |
| MPDA/$H_2SO_4$/$H_2O$ (mole ratio) | 1/2/60 | 1/2/60 | 1/2/60 |
| SINGLE PASS REACTION CONDITIONS | | | |
| Temperature (°C) | 240 | 240 | 240 |
| Time (hrs) | 1.5 | 3 | 6 |
| REACTION MIXTURE | | | |
| pH | 0.29 | 0.25 | 0.3 |
| Insoluble tars in the reactor (g) | 0 | 0 | 0.07 |
| Observation of insoluble tars (if present) | NA | NA | NA |
| CRUDE RESORCINOL | | | |
| Weight (g) | 50.1 | 53.2 | 52.3 |
| Resorcinol content (wt%, by NMR) | 99.1 | 99.7 | >99.9 |
| Soluble tar content (wt%, by NMR) | 0.9 | 0.3 | ND |
| Resorcinol yield (wt%) | 89.2 | 95.3 | 94 |
| AQUEOUS PHASE ANALYSIS | | | |
| ORGANIC MATERIALS (wt%, by NMR) | | | |
| Resorcinol | ND | ND | ND |
| *m*-Phenylenediamine | 0.1 | 0.1 | 0.1 |
| *m*-Aminophenol | 0.5 | 0.2 | 0.2 |
| Soluble tar | 0.2 | 0.1 | 0.1 |
| INORGANIC MATERIALS | | | |
| Ammonium bisulfate (wt%) | 18.7 | 18.2 | 18 |
| Ammonium sulfate (wt%) | 4.1 | 4.4 | 4.8 |

NA = Not Applicable
ND = None Detected

Figure 6

| Example | 24 | 25 | 26 | 27 | 28 |
|---|---|---|---|---|---|
| ZIRCONIUM REACTOR FEED (g) | | | | | |
| MPDA | 54.6 | 55.0 | 54.2 | 54.6 | 54.6 |
| $H_2SO_4$ | 99.1 | 94.8 | 103.4 | 99.1 | 99.1 |
| $H_2O$ | 546.2 | 550.1 | 542.4 | 546.2 | 546.2 |
| MPDA/$H_2SO_4$/$H_2O$ (mole ratio) | 1/2/60 | 1/1.9/60 | 1/2.1/60 | 1/2/60 | 1/2/60 |
| REACTION CONDITIONS | | | | | |
| Pass 1 | | | | | |
| Temperature (°C) | 230 | 230 | 230 | 230 | 230 |
| Time (hr) | 2 | 2 | 2 | 2 | 1 |
| Pass 2 | | | | | |
| Temperature (°C) | 230 | 230 | 230 | 230 | 230 |
| Time (hr) | 2 | 2 | 2 | 1 | 2 |
| REACTION MIXTURE | | | | | |
| Pass 1 | | | | | |
| pH | 0.26 | 0.38 | 0.28 | 0.31 | 0.31 |
| Insoluble tars in the reactor (g) | 0 | 0 | 0 | 0 | 0 |
| Pass 2 | | | | | |
| pH | 0.27 | 0.42 | 0.28 | 0.37 | 0.31 |
| Insoluble tars in the reactor (g) | 0 | 0 | 0 | 0 | 0 |
| CRUDE RESORCINOL | | | | | |
| Pass 1 | | | | | |
| Weight (g) | 45.1 | 47.4 | 41.9 | 44.1 | 26.3 |
| Resorcinol content (wt%, by NMR) | 98.2 | 97 | 98.8 | 98.2 | 96.9 |
| Soluble tar content (wt%, by NMR) | 1.8 | 2.9 | 1.2 | 1.8 | 3 |
| Resorcinol yield (wt%) | 79.6 | 82.1 | 74.9 | 77.8 | 45.8 |
| Pass 2 | | | | | |
| Weight (g) | 9.4 | 7.1 | 11.3 | 7.9 | 25.7 |
| Resorcinol content (wt%, by NMR) | >99.9 | 99.9 | 99.9 | 99.2 | 99.3 |
| Soluble tar content (wt%, by NMR) | ND | ND | ND | 0.6 | 0.7 |
| Resorcinol yield (wt%) | 16.9 | 12.6 | 20.4 | 14.2 | 45.8 |
| OVERALL RESORCINOL YIELD (wt%) (Pass 1 + Pass 2) | 96.5 | 94.7 | 95.3 | 92 | 91.6 |
| PASS 2 AQUEOUS PHASE ANALYSIS ORGANIC MATERIALS (wt%, by NMR) | | | | | |
| Resorcinol | ND | ND | ND | ND | ND |
| m-Phenylenediamine | ND | ND | ND | ND | 0.1 |
| m-Aminophenol | ND | 0.1 | 0.2 | 0.3 | 0.3 |
| Soluble tars | ND | 0.1 | 0.1 | 0.3 | 0.2 |
| INORGANIC MATERIALS | | | | | |
| Iron (ppm) | 8 | 2.4 | 2.9 | 5 | 3.4 |
| Ammonium bisulfate (wt %) | 18.2 | 16.6 | 19.3 | 18.3 | 18.5 |
| Ammonnium sulfate (wt %) | 3.8 | 4.3 | 4.3 | 4.2 | 4.0 |

ND = None Detected

Figure 7

| Example | 29 | 30 | 31 |
|---|---|---|---|
| STAINLESS STEEL REACTOR FEED (g) | | | |
| MPDA | 39.6 | 39.6 | 39.6 |
| $H_2SO_4$ | 64.6 | 64.6 | 64.6 |
| $H_2O$ | 395.8 | 395.8 | 395.8 |
| MPDA/$H_2SO_4$/$H_2O$ (mole ratio) | 1/1.8/60 | 1/1.8/60 | 1/1.8/60 |
| SINGLE PASS REACTION CONDITIONS | | | |
| Temperature (°C) | 240 | 220 | 220 |
| Time (hrs) | 2 | 3 | 6 |
| | | | |
| REACTION MIXTURE | | | |
| pH | 0.91 | 1.21 | 1.02 |
| Insoluble tars in the reactor (g) | 15 | 20.5 | 22.5 |
| Observation of insoluble tars (if present) | Heavy tar | heavy tar | heavy tar |
| Reactor weight loss during reaction (g) (initial weight = 3735 g) | 6.2 | 8.6 | 6.6 |
| CRUDE RESORCINOL | | | |
| Weight (g) | 24.9 | 22.1 | 24.3 |
| Resorcinol content (wt%, by NMR) | 92 | 85 | 90 |
| Soluble tar content (wt%, by NMR) | 7 | 13.3 | 8.1 |
| Resorcinol yield (wt%) | 56.9 | 46.6 | 54.3 |
| AQUEOUS PHASE ANALYSIS | | | |
| ORGANIC MATERIALS (wt%, by NMR) | | | |
| Soluble tar | 1.8 | 2.7 | 1.9 |
| INORGANIC MATERIALS | | | |
| Ammonium bisulfate (wt%) | 9.5 | 8.4 | 8.8 |
| Ammonium sulfate (wt%) | 1.3 | 2.6 | 1.7 |
| Iron (wt%) | 1.16 | 1.07 | 1.21 |

RESORCINOL PRODUCTION FROM THE HYDROLYSIS OF META-PHENYLENEDIAMINE

FIELD OF THE INVENTION

The present invention relates to a new process for preparation of resorcinol, using the meta-phenylenediamine hydrolysis reaction. A reactor vessel made of a suitable material such as zirconium or a zirconium alloy is used, thus resisting corrosion and formation of resinous materials.

BACKGROUND OF THE INVENTION

Resorcinol can be commercially produced by three different processes, namely, alkali fusion of meta-benzenedisulfonic acid, the hydroperoxidation process using meta-diisopropylbenzene, and the acid hydrolysis of meta-phenylenediamine. Since meta-phenylenediamine (MPDA) is commercially available, production of resorcinol is possible in a simple one-step acid hydrolysis process employing MPDA as the starting material. However, the MPDA hydrolysis process requires high temperature and strong acid catalysts. Employing strong acid catalysts in the presence of water brings the pH of the solution to a very low value. The combination of low pH and high temperature make the hydrolysis process dangerous and requires the use of non-corrosive materials to withstand these severe processing conditions.

When the reaction temperature is high, additional problems are encountered using the MPDA hydrolysis process. Resorcinol forms both water soluble and insoluble resinous products, or tars, at elevated temperatures in the presence of strong acids. These resinous products can be the result of resorcinol reacting with other materials present in the reaction mixture, including the starting materials (such as MPDA) or reaction intermediates such as m-aminophenol (MAP). In addition, resorcinol has the tendency to produce polyaryl ether-type structures under these hydrolysis process conditions. The insoluble resinous materials can build up in the reactor, making frequent cleaning necessary. In continuous operations, they can block process lines, resulting in a potentially hazardous situation. Additionally, the formation of resinous products tends to reduce the final resorcinol yield from this process. Therefore, it is important to develop a process that does not produce any resinous or insoluble material during the hydrolysis reaction.

Several attempts have been made in the past to develop a cost-effective and simpler process for the manufacture of resorcinol from the acid hydrolysis of MPDA. For example, U.S. Pat. No. 3,462,497 discloses the hydrolysis of MPDA using ortho-phosphoric acid or $H_2SO_4$ in an autoclave fitted with a Monel liner. From the data presented in the examples, it is evident that a resinous-type product was produced during the hydrolysis process.

U.S. Pat. No. 3,862,245 discloses a process to prepare resorcinol from the MPDA hydrolysis using $H_2SO_4$ in a tantalum tubular reactor surrounded by an oil bath; a resorcinol yield of 67.5 wt. % was achieved with an $H_2SO_4$/MPDA molar ratio of 1.6:1.

Japanese Patent Disclosure S52-153919 discloses that a very high resorcinol yield can be achieved with hydrochloric acid in a Hastelloy B type reactor. Use of $H_2SO_4$ resulted in a significant decline in resorcinol yield.

U.S. Pat. No. 3,862,246 discloses the use of ammonium bisulfate as an acid for the hydrolysis of MPDA to produce resorcinol. Use of large amounts of salt is uneconomical and results in handling difficulties during the manufacturing process.

There is a continued need for the development of a simple and cost-effective method of preparing resorcinol, using the MPDA hydrolysis reaction.

SUMMARY OF THE INVENTION

The present invention solves the above need by providing a method of making resorcinol using the MPDA hydrolysis process, in a reactor vessel made of zirconium, a zirconium alloy or other suitable material as will be defined herein. Sulfuric acid and meta-phenylenediamine in an aqueous solution are placed in the reactor vessel and heated, while stirring, for a period of time sufficient to complete the hydrolysis reaction and then cooled to room temperature. After cooling, the resorcinol can be extracted from the aqueous solution with an organic solvent. It has been found that a zirconium or zirconium alloy reactor vessel is particularly resistant to corrosion and able to withstand the severe processing conditions required by the MPDA hydrolysis process. Other materials, such as gold, molybdenum, platinum, titanium, and tungsten, as well as alloys containing these materials, are also expected to provide corrosion resistance along with the ability to withstand the severe processing conditions. This reduction in corrosion contributes to the reduction of tarry, resinous materials, because metal corrosion products which can catalyze the formation of the tarry residue are not present in the reactor vessel. Additionally, use of stirring during the heating process, in combination with the proper molar ratios of $H_2SO_4$ and MPDA, further limits the formation of resinous materials.

It is an object of the present invention, therefore, to develop a cost-effective resorcinol manufacturing process using the MPDA hydrolysis reaction.

It is an additional object of the present invention to improve the resorcinol yield using the MPDA hydrolysis reaction.

It is an additional object of the present invention to use the MPDA hydrolysis reaction with a suitable reactor vessel to avoid corrosion and formation of tar or other resinous by-products during the hydrolysis reaction.

These and other objects will be more fully understood from the following detailed description, examples and appended claims.

BRIEF DESCRIPTION OF THE DRAWING

The invention is further illustrated by the following non-limited figures in which.

DETAILED DESCRIPTION OF THE PREFERRED EMBODIMENTS

In accordance with the present invention, meta-phenylenediamine is hydrolyzed in a aqueous medium, through the use of sulfuric acid, to produce resorcinol. The reaction is carried out in a suitable reactor vessel, which is able to withstand corrosion and high reaction temperatures. A molar ratio of about 1.6 to 2.1 moles sulfuric acid to about 1.0 moles MPDA is used, preferably about 1.8 moles of sulfuric acid to every mole of MPDA, more preferably about 2.0 moles of sulfuric acid to every mole of MPDA. These molar ratios ensure sufficient conversion of the starting materials and provide the highest yield of resorcinol.

The hydrolysis can be carried out in one step or it can be continued sequentially with additional passes. A one-step hydrolysis is desirable from the standpoint of ease and efficiency of operation, although an increase in yield can be achieved by a second hydrolysis of the reaction mixture after removing the product from the first hydrolysis.

Water must be present in an amount sufficient to provide for hydrolysis and also to serve as a diluent or solvent for the meta-phenylenediamine and sulfuric acid during the course of the reaction. Typically, about 50–120 moles of water per mole of MPDA are used, more preferably 55–80 moles, most preferably 55–65 moles, as sufficient water must be present to dissolve the desired quantities of the reaction ingredients.

The reaction temperature must be maintained over a range of between about 200°–250° C., more preferably 225°–235° C. Insufficient yield results from temperatures which are too low, while temperatures above this range result in excessive decomposition or by-product formation. Temperatures in excess of 250° C. have resulted in $SO_2$ formation, which indicates that the sulfuric acid is acting as an oxidant rather than as a hydrolyzing agent at these higher temperatures.

The reaction time will vary with the temperature and exact molar ratio of the reactants; the hydrolysis reaction will typically be complete within about 2 to 10 hours. A reaction time of about 6 hours is preferred for complete hydrolysis and prevention of formation of resinous materials. As used herein, "a time sufficient to complete the hydrolysis reaction" refers to the above described ranges, which will vary depending on the exact molar ratios and temperature used.

The starting materials are charged to a reactor vessel which is then purged with $N_2$ and sealed. Hydrolysis is carried out in a reactor vessel which can provide suitable resistance to corrosion and withstand the severe processing conditions required for the hydrolysis reaction. Preferred materials for the reactor vessel include, but are not limited to, gold, molybdenum, platinum, titanium, tungsten, and zirconium, as well as alloys containing these compounds. As used herein, the term "suitable reactor vessel material" will be understood to include any of these materials. Most preferred is a reactor vessel made of zirconium or a zirconium alloy, as these materials have been found to resist corrosion and provide an optimal environment for production of resorcinol. As used herein, the term "zirconium reactor vessel" will refer to a vessel formed entirely of zirconium or a zirconium alloy, or a vessel having an internal chamber that is substantially clad with zirconium or a zirconium alloy, and additionally may have zirconium or zirconium alloy internal components such as a stirrer, thermowell, and the like. Preferably, the reactor vessel is equipped with a stirrer, and the reaction mixture is stirred continuously during the course of the reaction. It is thought that the stirring of the reaction mixture during the reaction aids in the reduction of resinous by-products, although the inventors do not wish to be bound by this.

After the reaction is sufficiently complete, the reaction mixture is cooled to ambient temperature to prevent resinification of the product in the aqueous reaction mixture and to enable the extraction of resorcinol with an organic solvent. Any substantially water immiscible organic solvent which will dissolve resorcinol can be used. Suitable solvents include alcohols such as n-butanol; ethers such as diethyl ether, dimethyl ether and diphenyl ether; aromatics such as benzene, toluene, chlorobenzenes and nitrobenzene; chlorinated hydrocarbons such as methylene chloride, chloroform and trichloroethylene; aliphatic hydrocarbons such as cyclohexane, petroleum ether and the like. Diethyl ether is preferred.

The organic solvent phase is then separated from the reaction mixture by decantation and the solvent is removed from the resorcinol product by distillation.

After removal of the resorcinol product, the resulting effluent reaction mixture can be reheated to the hydrolysis temperature for a second or even a third hydrolysis step. The second and subsequent hydrolysis steps are carried out as before by heating the reaction mixture to the appropriate temperature of hydrolysis for the desired period of time, cooling and removing the product resorcinol by solvent extraction.

The invention is further illustrated by the following nonlimiting examples.

EXAMPLE 1

Synthesis of Resorcinol from the Single-Pass MPDA Hydrolysis Reaction at 200° C. Using Zirconium Reactor In a 1-liter zirconium reactor equipped with a stirrer, thermocouple and pressure gauge, 0.5 mole (54.0 grams) of m-phenylenediamine (MPDA), 0.8 mole (78.4 grams) of sulfuric acid ($H_2SO_4$) and 30 moles (540 grams) of distilled water were charged. The molar ratio of MPDA:$H_2SO_4$ was 1:1.6. The reactor was purged with nitrogen and heated to 200° C. temperature. The reaction mixture was held at 200° C. for a period of 2.0 hours and cooled slowly to room temperature. The visual observation of aqueous reaction product appeared clear, and no insoluble tar material was seen in the solution that had a pH of 0.61. The aqueous solution was extracted with ether. Finally, the ether was distilled out to obtain 11.0 grams of crude resorcinol. Purity of the crude resorcinol was checked by NMR analysis and showed 91.4 wt. % resorcinol, corresponding to a resorcinol yield of 18.4 wt. %. Analysis of the crude product also indicated the presence of tarry materials at 8.4 wt. % level.

Analysis of Tars Present in the Crude Resorcinol

FT-IR and NMR analysis techniques were utilized to characterize the nature of tar materials present in the crude resorcinol product. The analysis data suggested the following structure for the tar:

This compound, 3,3'-dihydroxy diphenylamine, can be produced from the reaction of m-aminophenol and resorcinol in the presence of strong acids such as $H_2SO_4$ and $NH_4HSO_4$. The presence of this organic impurity in the crude resorcinol suggests the formation of more m-aminophenol (MAP) type structures during hydrolysis.

Analysis of Aqueous Solution After Ether Extraction

FT-IR, NMR and wet analysis techniques were used to characterize the nature and amounts of organic and inorganic materials present in the aqueous phase obtained after the ether extraction of the MPDA hydrolysis product. The details are given below:

| Organic/Inorganic Component | Wt. % |
|---|---|
| 1. MPDA | 2.2 |
| 2. MAP | 2.7 |
| 3. Diphenylamine Tars | 1.5 |
| 4. $(NH_4)_2SO_4$ | 4.0 |
| 5. $NH_4HSO_4$ | 16.1 |

Organic impurities such as MPDA, MAP and diphenylamine tars are present in the form of salts.

EXAMPLES 2 THROUGH 8

A series of single-pass type experiments were run following the conditions described in Example 1 with varying molar ratios of $H_2SO_4$ and water. During these experiments, the temperature of hydrolysis was kept constant at 200° C. The results are summarized in FIG. 2.

Figure 2:
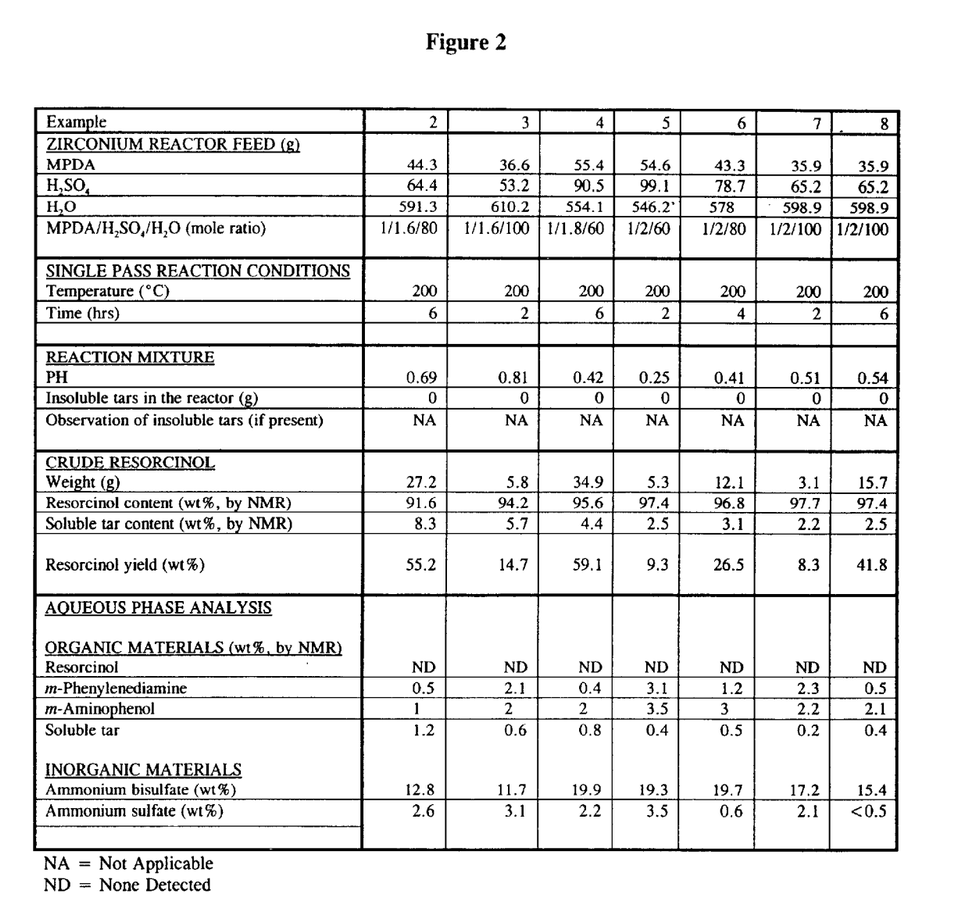
FIG. 2 contains data from single pass MPDA hydrolysis reactions at 200° C.

From the results of FIG. 2, it is clear that no insoluble tar was seen in the aqueous hydrolysis product. The resorcinol yield appeared to be low, indicating that hydrolysis was not complete due to low temperature (200° C.). Analysis of the crude resorcinol product showed high amounts of tar when a lower molar concentration of $H_2SO_4$ was used. Tar production appeared to decrease as the $H_2SO_4$/MPDA (mole) ratio increased from 1.6 to 2.0.

The zirconium reactor used in the hydrolysis process was weighed each time before and after the reaction for any weight loss due to corrosion. In all the experiments, the weight of the zirconium reactor vessel remained unchanged indicating no corrosion occurred in spite of low pH (pH<1.0) and high temperature ($\geq$200° C.) hydrolysis conditions.

EXAMPLES 9 THROUGH 12

A second series of single-pass experiments was run using the same zirconium reactor vessel as described in Example 1. The hydrolysis temperature was kept at 215° C. to determine the effectiveness of hydrolysis and the corrosion behavior of the zirconium vessel at this temperature. The $H_2SO_4$/MPDA molar ratio, water content and hydrolysis times were varied in these experiments. The results are summarized in FIG. 3.

Figure 3:
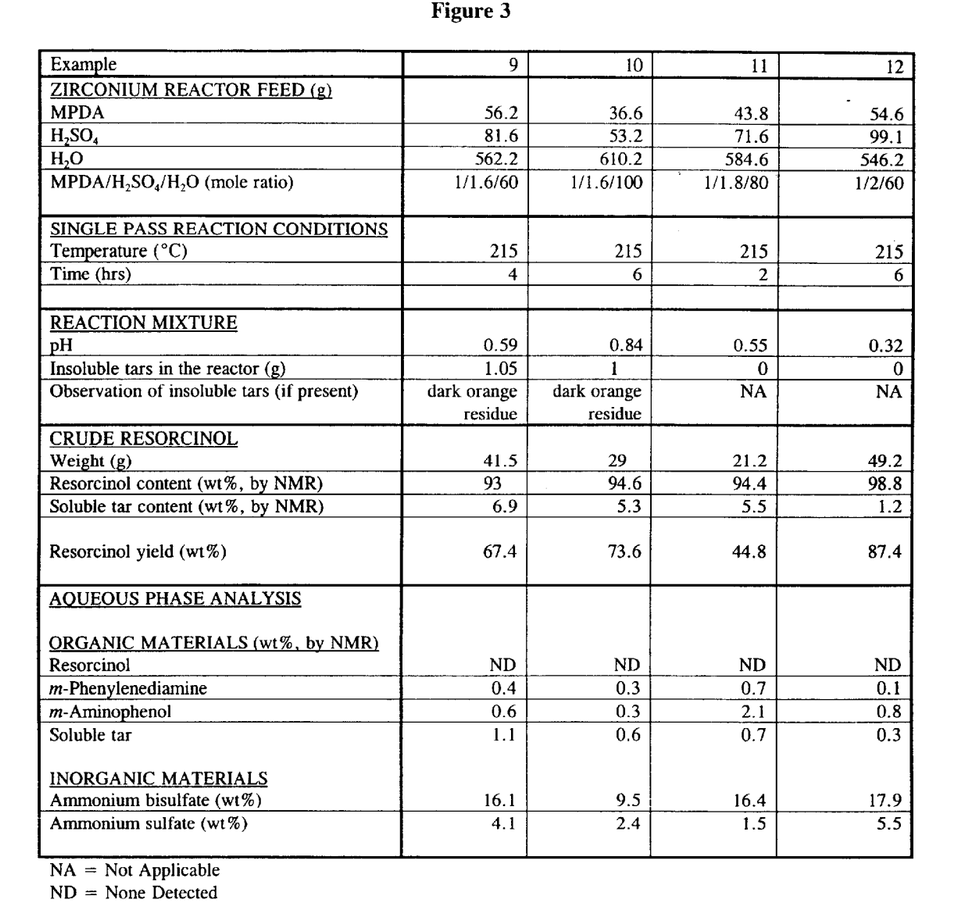
FIG. 3 contains data from single pass MPDA hydrolysis reactions at 215° C.

When the molar ratio of $H_2SO_4$/MPDA was increased from 1.6 to 2.0, the resorcinol yield was dramatically increased from 67.4 to 87.4 wt. %. The amount of tar present in the crude resorcinol also decreased.

No insoluble tar was seen in the hydrolysis product when the $H_2SO_4$/MPDA ratio was 1.8 or higher. Careful weighing of the zirconium reactor before and after the reaction indicated no corrosion at a 215° C. temperature.

EXAMPLES 13 THROUGH 20

Figure 4:
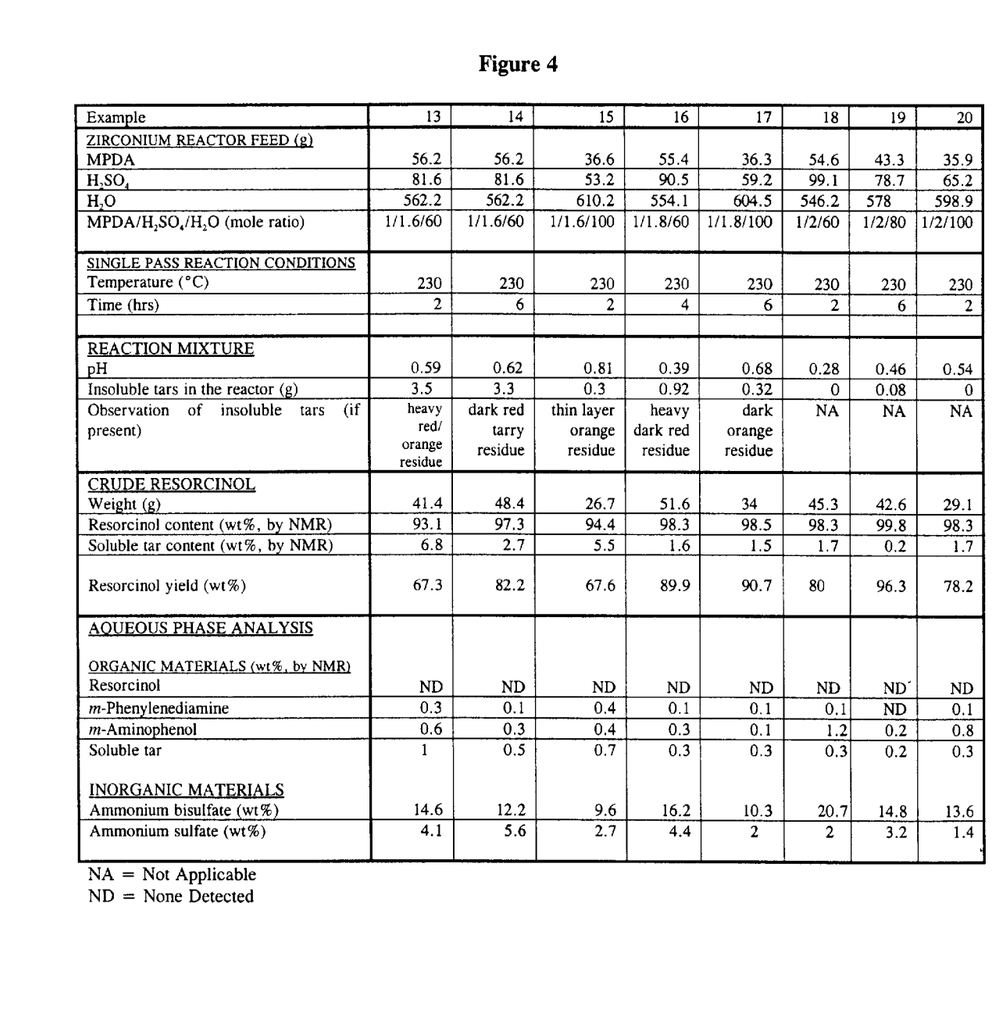
FIG. 4 contains data from single pass MPDA hydrolysis reactions at 230° C.

A third series of single-pass experiments was run at 230° C. temperature conditions to determine the corrosion resistance of the zirconium vessel and the effectiveness of the hydrolysis process. The experimental results are given in FIG. 4. As can be seen from the data presented in FIG. 4, the aqueous hydrolysis product contained tarry insoluble material when the $H_2SO_4$/MPDA ratio was 1.6 and decreased to almost no tar when the $H_2SO_4$/MPDA ratio was 2.0. A high resorcinol yield of 96.3 wt. % was achieved in a single-pass hydrolysis reaction carried out for 6.0 hours, with a very small amount of tar residue present in the crude resorcinol.

The resorcinol yield from the process of this invention is significantly higher than other MPDA/$H_2SO_4$ hydrolysis processes and procedures reported in the literature.

EXAMPLES 21 THROUGH 23

In order to investigate the hydrolysis process and also determine the corrosion behavior of the zirconium vessel at elevated temperatures, a fourth series of single-pass experiments was carried out using a fixed $H_2SO_4$/MPDA/$H_2O$ (mole) ratio and 240° C. temperature conditions. The reaction time was varied. Results are summarized in FIG. 5.

Figure 5:
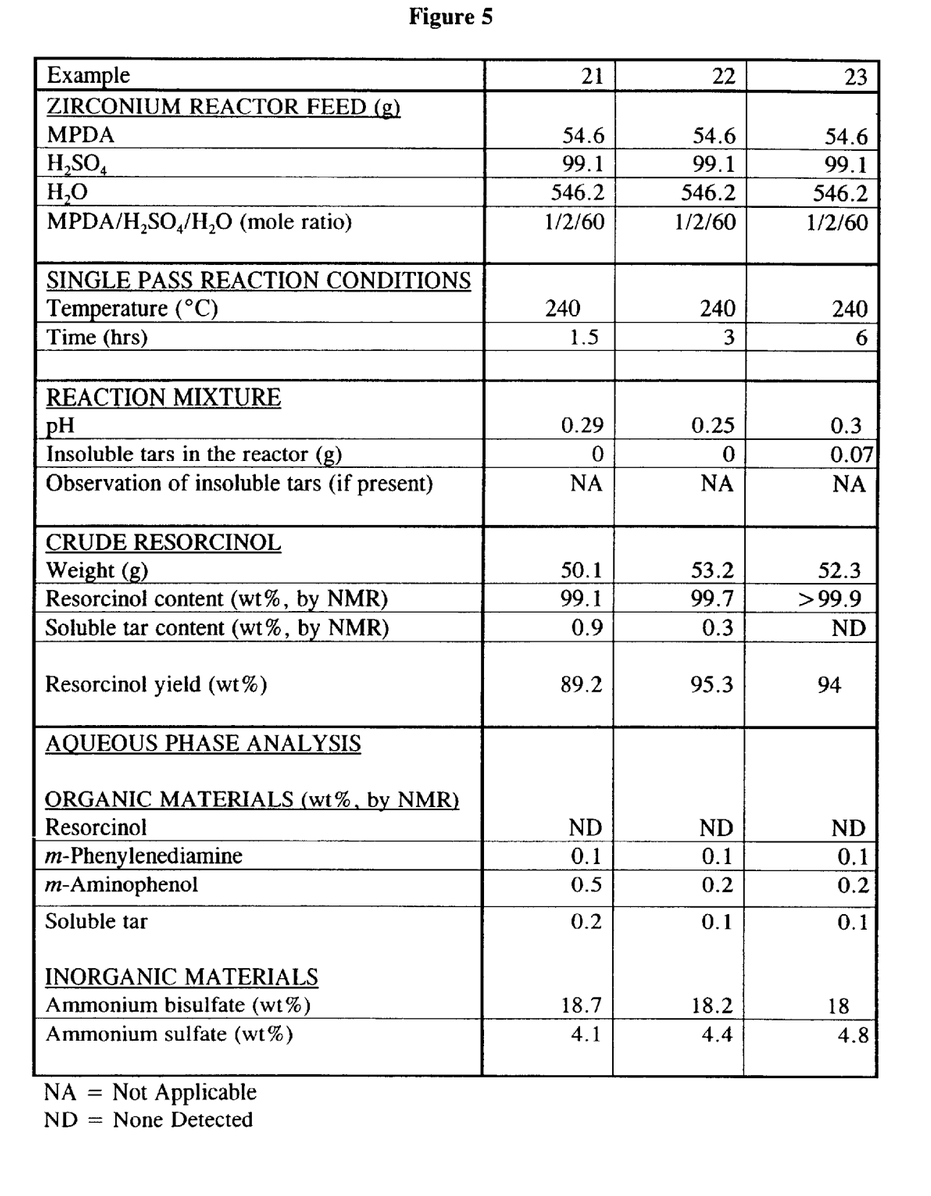
FIG. 5 contains data from single pass MPDA hydrolysis reactions at 240° C.

The zirconium reactor vessel did not show any changes in weight before and after the hydrolysis reaction, indicating high corrosion resistance of this vessel, in spite of a very high hydrolysis temperature for as long as six hours. MPDA-$H_2SO_4$ hydrolysis is very effective and smooth at a $H_2SO_4$/MPDA molar ratio of 2.0, based on the high resorcinol yield and lack of insoluble tar in the hydrolysis product.

EXAMPLE 24

Synthesis of Resorcinol from the 2-Pass MPDA/$H_2SO_4$ Hydrolysis Reaction Using a Zirconium Reactor A solution of m-phenylenediamine (54.62 grams, 0.506 mole), sulfuric acid (99.18 grams, 1.012 mole) and water (576.8 grams, 30.36 moles) was prepared and placed in a zirconium pressure reactor fitted with a mechanical stirrer, thermocouple and pressure gauge. The mole ratio of MPDA/$H_2SO_4$/$H_2O$ was 1/2/60. The reactor was purged with nitrogen to displace the oxygen present inside the reaction. The reactor contents were then heated to 230° C., with constant stirring for a period of 2.0 hours. At the end of the reaction period, the reaction mixture was cooled to room temperature. Visual observation of the reaction product showed an absence of insoluble tar or tarry products. The reaction mixture was then extracted two to three times with ether. The ether extract was distilled to obtain a crude resorcinol residue weighing 45.1 grams labeled as "Pass-1". NMR analysis of the crude resorcinol showed 98.2 wt. % resorcinol and 1.8 wt. % tar present in Pass-1 material, corresponding to a resorcinol yield of 79.6 wt. %.

The aqueous phase, after the Pass-i ether extraction, contained dissolved ether. The dissolved ether was removed and then the aqueous phase was charged to the zirconium reactor and heated for 2.0 hours at 230° C. temperature (Pass-2 reaction). At the end of reaction, the Pass-2 reaction mixture was cooled to room temperature; no visual insoluble or tarry products were observed to be present either in the solution or inside the zirconium reactor. The Pass-2 reaction product was ether extracted as before and the extract was distilled to obtain 9.0 grams of crude resorcinol. Crude resorcinol obtained from Pass-2 was analyzed by NMR and showed >99.9 wt. % resorcinol, corresponding to a 16.9 wt. % resorcinol yield.

Therefore, the total resorcinol yield from the Pass-1 (79.6 wt. %) and Pass-2 (16.9 wt. %) MPDA hydrolysis process of the present invention was 96.5 wt. %.

Figure 1:
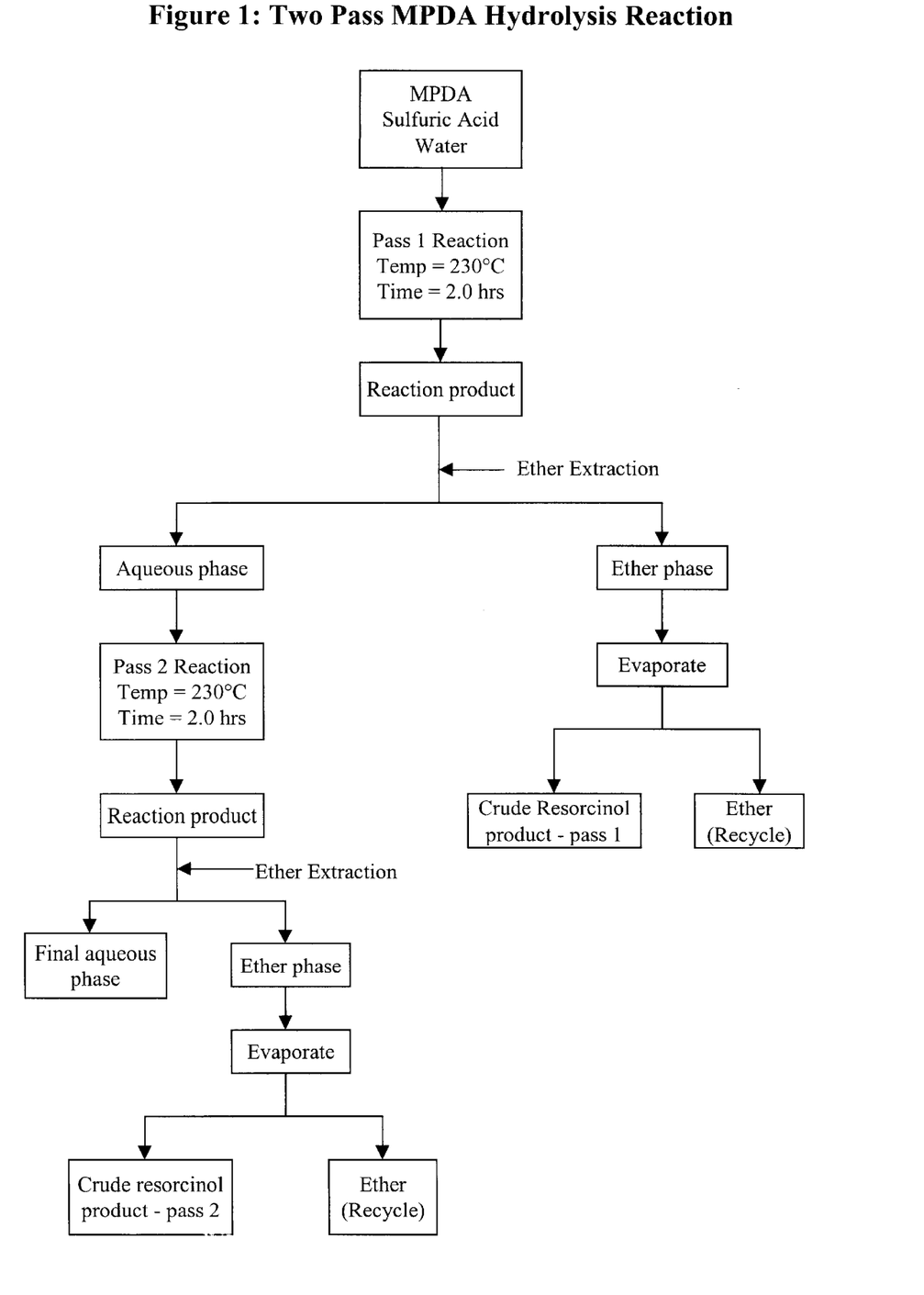
FIG. 1 is a flow diagram in which the steps of the MPDA hydrolysis reaction are provided.

The zirconium reactor was weighed accurately before and after the hydrolysis reaction and found unchanged indicating no corrosion to the reactor even though a high temperature and low pH solution conditions were employed. FIG. 1 shows the schematic diagram of the 2-Pass reaction of the MPDA hydrolysis process of this invention.

EXAMPLES 25 THROUGH 28

Figure 6:
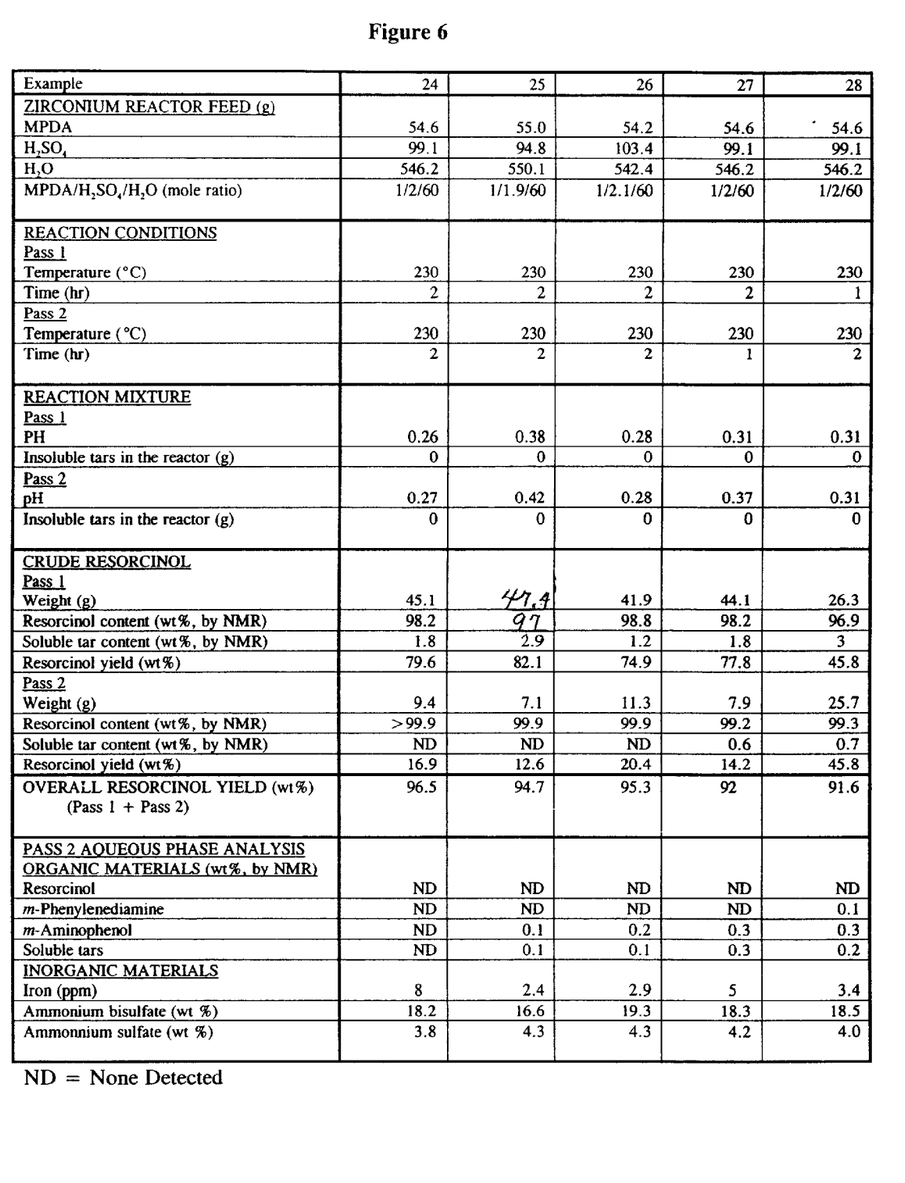
FIG. 6 contains data from two pass MPDA hydrolysis reactions at 230° C.

Following the conditions of Example 24, a series of 2-Pass MPDA hydrolysis reactions were done employing slight changes in $H_2SO_4$/MPDA mole ratios and reaction times during the Pass-1 and Pass-2 operations. The details are summarized in FIG. 6 along with Example 24 results.

A resorcinol yield in excess of 90.0 wt. % is easily achieved using the process of the present invention.

Comparative Examples

EXAMPLES 29 THROUGH 31

Figure 7:
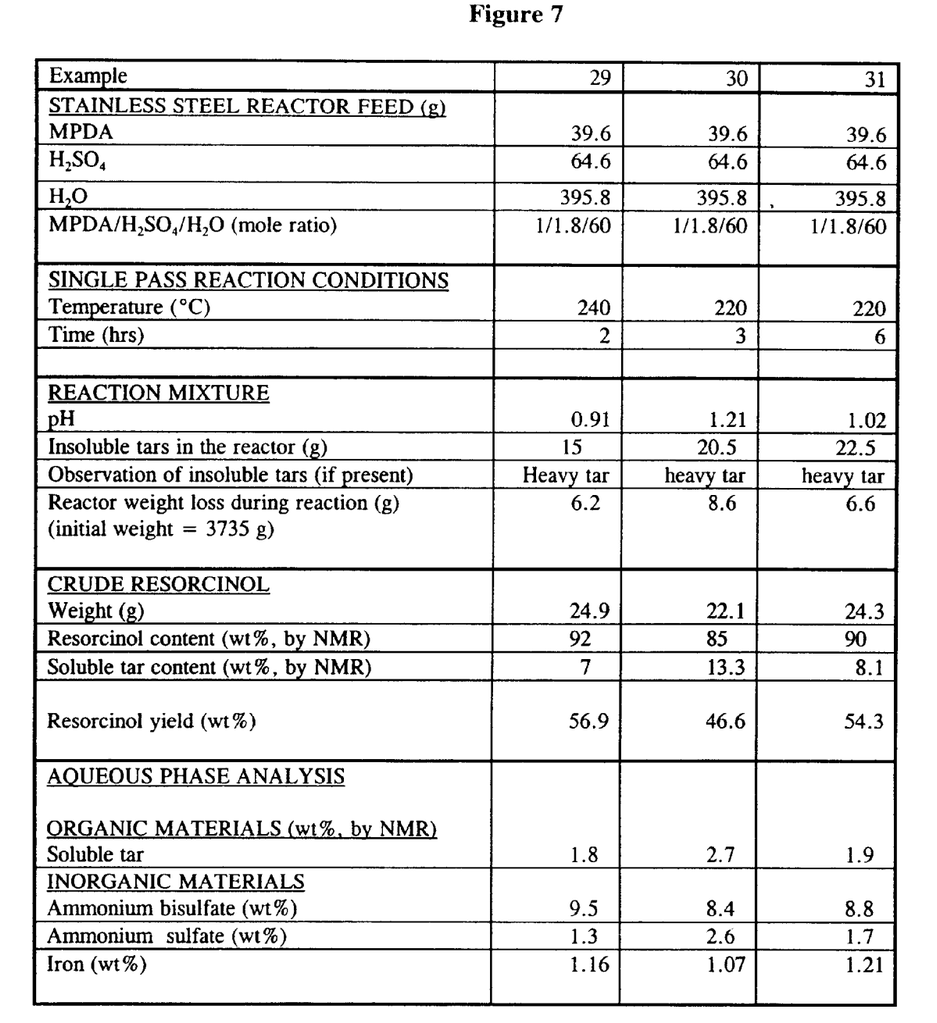
FIG. 7 contains data from single pass MPDA hydrolysis reactions in a stainless steel reactor.

A stainless steel Parr reactor was charged with MPDA, $H_2SO_4$ and water at a molar ratio of 1/1.8/60. The hydrolysis reactions, separation of products, analysis of crude resorcinol and aqueous phase were performed similarly as mentioned in the single-pass reactions carried out using the zirconium reactor. The details are given in FIG. 7. As seen by the significant weight loss of the vessel during the reaction, severe corrosion to the stainless steel reactor was observed. An insoluble tarry product came out of the reaction mixture and appeared to stick to the walls of the reactor. The final resorcinol yield was low and contained higher levels of high boiling, tar-type materials. These observations indicate that a standard stainless steel reactor or vessel is unsuitable for an acid hydrolysis of MPDA.

While particular embodiments of this invention have been described above for purposes of illustration, it will be evident to those skilled in the art that numerous variations of the details of the present invention may be made without departing from the invention as defined in the appended claims.

What is claimed is:

1. A method of making resorcinol comprising:
   (i) charging sulfuric acid and meta-phenylenediamine in an aqueous solution to a reactor vessel made of a suitable material;
   (ii) purging said reactor vessel with $N_2$ and sealing said vessel;
   (iii) heating said aqueous solution in said reactor vessel to initiate a hydrolysis reaction, and continuing said heating for a period sufficient to complete the hydrolysis reaction;
   (iv) cooling said aqueous solution; and
   (v) extracting said resorcinol from said aqueous solution with an organic solvent,
   said suitable reactor vessel material selected from the group consisting of gold, platinum, titanium, tungsten, zirconium and alloys thereof.

2. The method of claim 1, wherein said reactor vessel material is selected from the group consisting of zirconium and a zirconium alloy.

3. The method of claim 1, wherein the molar ratio of sulfuric acid to the meta-phenylenediamine is about 1.6–2.1:1.

4. The method of claim 1, wherein said aqueous solution comprises about 50 to 120 moles of water.

5. The method of claim 1, wherein a reaction temperature is maintained between about 200°–250° C.

6. The method of claim 1, wherein said aqueous solution is continuously stirred during said heating period.

7. The method of claim 1, wherein said heating period is between about 2–10 hours.

8. The method of claim 1, wherein said organic solvent is ether.

9. The method of claim 1, further comprising evaporating said organic solvent to obtain crude resorcinol.

10. The method of claim 1, after said resorcinol extraction, further comprising:
   (i) removing said organic solvent from said aqueous solution;
   (ii) charging said aqueous solution to said reactor vessel;
   (iii) purging said reactor vessel with $N_2$ and sealing said vessel;
   (iv) heating said aqueous solution in said reactor vessel to initiate a hydrolysis reaction, and continuing said heating for a period of time sufficient to complete the hydrolysis reaction;
   (v) cooling said aqueous solution; and
   (vi) extracting said resorcinol from said aqueous solution with an organic solvent.

11. The method of claim 10, further comprising evaporating said organic solvent to obtain crude resorcinol.

* * * * *

UNITED STATES PATENT AND TRADEMARK OFFICE
CERTIFICATE OF CORRECTION

PATENT NO.    : 6,531,637 B1
DATED         : March 11, 2003
INVENTOR(S)   : Raj B. Durairaj et al.

It is certified that error appears in the above-identified patent and that said Letters Patent is hereby corrected as shown below:

Column 6,
Line 52, "Pass-i" should read -- Pass-1 --.

Signed and Sealed this

Twenty-ninth Day of April, 2003

JAMES E. ROGAN
*Director of the United States Patent and Trademark Office*